United States Patent [19]

Manning et al.

[11] Patent Number: 4,755,421

[45] Date of Patent: Jul. 5, 1988

[54] HYDROENTANGLED DISINTEGRATABLE FABRIC

[75] Inventors: James H. Manning, Appleton, Wis.; Joseph H. Miller, Greenville; Thomas E. Quantrille, Simpsonville, both of S.C.

[73] Assignee: James River Corporation of Virginia, Richmond, Va.

[21] Appl. No.: 82,512

[22] Filed: Aug. 7, 1987

[51] Int. Cl.$^4$ .............................................. B32B 3/10
[52] U.S. Cl. ..................................... 428/224; 28/104; 428/292
[58] Field of Search ............... 428/224, 288, 290, 292, 428/300; 28/104

[56] References Cited

U.S. PATENT DOCUMENTS 4,117,187  9/1978  Adams et al. ...................... 428/288
4,612,226  9/1986  Kennette et al. ................... 428/224

Primary Examiner—Marion C. McCamish
Attorney, Agent, or Firm—Richard J. Gallagher

[57] ABSTRACT

A nonwoven fibrous web is disclosed having high wet tensile strength when packed in a preservative liquid load, yet which breaks up under mild agitation conditions in a wet environment such as by the flushing action of a toilet. The wiper includes a nonwoven web made of a special blend of cellulosic fibers held together only by friction and naturally occurring hydrogen bonding. No binder is necessary to hold together the fibers. Derivatization of the fibers is not necessary for their breakapartability. The nonwoven fibrous web is produced by subjecting a wet-laid web of cellulosic fibers to hydroentanglement and drying the web without addition of a bonding agent.

13 Claims, No Drawings

HYDROENTANGLED DISINTEGRATABLE FABRIC

This invention relates to nonwoven fibrous webs and, more particularly, to an improved nonwoven fibrous web which has sufficient wet strength to be used as a wet wiper, yet which is biodegradable and capable of disintegration when disposed of through a plumbing system after use. This invention also relates to a method for the manufacture of said web.

One aspect of the present invention relates to a unique blend of fiber furnish comprising a synthetic fiber component coupled with a pulp fiber component.

Another aspect of this invention relates to the application of particular hydroentanglement conditions to a nonwoven fiber substrate to provide sufficient entanglement of fibers for adequate wet strength to permit the substrate to be used as a wet wiper, yet allowing it to break apart rapidly under the mild agitation of conventional plumbing systems so that the wiper can be safely disposed of after use by flushing it through a toilet.

A further aspect of the present invention relates to a method for forming a nonwoven fibrous web from a dispersion of pulp and synthetic fibers and use of hydroentanglement energy to lock the fibers together into a web having sufficient wet strength to be used as a wet wiper, yet which is biodegradable and capable of rapid disintegration when the wiper is disposed of through a plumbing system after use.

Wet wipers are commonly used by consumers for cleansing or wiping parts of the body, especially where wash water is not readily available or cannot be used conveniently; they are particularly convenient for travelers. Wet wipers frequently complement, and occasionally substitute for, dry toilet paper. They can be used to apply or remove facial makeup as well. Because of the nature of such uses, wet wipers are often disposed of in a sewer system after use by flushing through a toilet.

Typically, a wet wiper is a nonwoven web of fibrous material including natural and synthetic fibers bonded together by a binder material having good adhesive qualities when the wiper is immersed in a liquid used to pre-moisten or wet the web. Usually, it is stacked and wrapped in a liquid-tight package while maintained in a liquid preservative composition containing an antimicrobial agent comprising about 50 to 300 percent by weight of the dry wiper weight. The wetting liquid can include water and often it will contain bactericides and other biological control agents, as well as perfumes and emulsifiers to disperse those ingredients, and it may be maintained at an acid pH level to further inhibit growth of organisms over sufficiently long time periods that can be experienced for warehousing, transportation, retail display, and storage of the wet wiper.

As an anal cleansing tissue, for example, the wet wiper must have sufficient strength to resist tears and punctures through use. Moreover, it must be capable of retaining its strength in a moist environment over a minimum shelf life of 2 to 6 months and preferably as long as 1 or 2 years.

Conventional techniques for achieving disintegration of prior art wipers in the flush water rely on chemical action for their effectiveness, such as by utilizing pH sensitive, water-soluble fiber binder adhesives. These binders exhibit a resistance to weakening in acid pH, but a high enough pH causes the binder to lose its adhesiveness and allows disintegration of the wiper to occur. Because environmental pH conditions vary greatly from one geographical location to another, flush water is not universally neutral or alkaline in nature but can be acidic. In those instances, the pH level is too low for the binder to become soluble or to be neutralized and the wiper does not disintegrate after flushing. Because such wet wipers do not readily disintegrate in the sewer system, their disposal in this manner can result in a plugged drain or sewer lateral.

A nonwoven fibrous web in accordance with the present invention has sufficient wet strength to be used as a wet wiper, yet is capable of disintegrating readily in flush water via mechanical action regardless of water composition to allow for flushability and minimal obstruction of plumbing systems. A wet wiper prepared from the nonwoven web of this invention is comprised of cellulosic fibers which are neither bonded by adhesive as disclosed in U.S. Pat. No. 4,117,187 nor chemically modified as disclosed in U.S. Pat. No. 3,546,755.

U.S. Pat. No. 3,546,755 discloses a nonwoven fabric strong enough to be a diaper or other single-use absorbent device, yet disintegrable enough to be disposable in a sewer system after use. The nonwoven fabric is formed of a web of regenerated cellulose fibers which are entangled together using fine columnar streams of water delivered under high pressure to the web. The fibers are phosphorylated or chemically modified with phosphate ester groups and a buffered sodium salt solution so that the fibers become slippery when wet with water to permit the fabric to break up in the flush water.

According to U.S. Pat. No. 4,117,187, a nonwoven web of fibrous material is bonded together by a polymeric binder which loses its adhesiveness in neutral or alkaline water to allow for flushability.

SUMMARY OF THE INVENTION

The present invention overcomes previous problems in the art and achieves various advantages by providing a nonwoven fibrous web of cellulosic fibers hydraulically entangled together with sufficient energy for adequate strength to process the web into a premoistened towelette or wet wiper, for example, including one-time use of the wiper thereafter, and to permit disentanglement of the fibers when the wiper is exposed to the mild agitation of conventional plumbing systems so that the wiper can be safely disposed of after use by flushing it through a toilet.

This invention provides a nonwoven fibrous web having a basis weight in the range of 20 to 90 grams per square meter having sufficient wet strength in an aqueous environment for use as a wet wiper capable of disintegrating under mild agitation in water and decomposing in a septic system. At least 70 weight percent wood pulp fibers and at least 5 weight percent short, staple length regenerated cellulose fibers are hydroentangled together to form a composite web having a wet tensile strength of at least 250 grams per inch. The fibers are bonded together only by friction and by naturally occurring hydrogen bonding.

The nonwoven fibrous web of the present invention is produced by forming a dispersion consisting essentially of 5 to 30 weight percent short, staple length regenerated cellulose fibers and 70 to 95 weight percent softwood papermaking fibers in an aqueous carrier medium, forming a wet web of the fibers on a foraminous member, entangling the fibers in the web with one another by hydroentanglement with sufficient energy to impart a wet tensile strength of at least 250 grams per inch to the web, and then drying the web without the addition of a bonding agent.

These and other features and advantages of the present invention will be more apparent from the following description of the preferred embodiments.

DESCRIPTION OF THE PREFERRED EMBODIMENTS

In accordance with the present invention, a nonwoven fibrous web is provided for use as a wet wiper, for example, having sufficient wet strength in an aqueous environment maintainable over a relatively long period of shelf life, including subsequent use of the wiper, and which is further capable of disintegrating and decomposing when flushed through a toilet.

The aqueous environment for the wet wiper can be selected from various conventionally known formulations that control pH and bacteria growth which may contain perfumes, alcohols, emulsifiers, and surfactants.

The pulp component of the present invention can be selected from any class of pulp and blends thereof. Preferably, the pulp fiber is characterized by a thin wall or small diameter and low fines. Although we prefer to use Northern softwood papermaking pulp (e.g. spruce, hemlock, cedar and pine), hardwood pulp and non-wood pulp (e.g. hemp and sisal) may be used.

The nonwoven web also contains an important concentration of synthetic fibers with preferred length and denier. Preferably, the web is formed from an intimate blend of short cut, synthetic, cellulosic fibers blended with the pulp. A typical synthetic cellulosic fiber is rayon. Generally, good tensile strength is obtained with 5 to 30 weight percent of 1.5 denier×12.5 millimeter rayon in blend with 70 to 95 weight percent softwood pulp if the substrate is entangled under proper conditions.

The synthetic fiber component of the present invention is not limited only to rayon but can be other cellulosic fibers, for example, cellulose acetate and hollow rayon (ie, viscose rayon injected with carbonates). Non-cellulosic synthetic fibers can be used to achieve the required strength and disintegration of the web, but with a comprise to the complete biodegradability of the web. Among the non-cellulosic synthetic fibers which may be used according to the present invention are fibers made from polyesters, polyolefins, polysaccharides (eg. calcium alginate), nylons and acrylics. The synthetic fiber component of the present invention can also be a blend of these fibers.

The basis weight of the web can be as low as about 20 grams per square meter to as high as about 90 grams per square meter. The lower limit generally defines the minimum basis weight necessary so that the web can be satisfactorily processed into a wet wiper. The upper limit is somewhat arbitrary and represents an approximate basis weight greater than which the web will probably be too costly to be commercialized. Preferably, the basis weight of the web is in the range of 60 to 75 grams per square meter.

The web can be formed by any common web manufacturing process. It can be produced by a conventional wet laying and wet creping process, or by wet laying and through air drying, or by air laying the web, or by other techniques utilized in the paper and nonwovens industries such as those used to produce toweling and tissue paper.

Preferably, the nonwoven fibrous web is produced by a classical, wet-laid papermaking method using any one of various, commonly practiced dispersant techniques to disperse a uniform distribution of rayon and wood pulp fibers onto a foraminous screen of a conventional paper making machine. U.S. Pat. Nos. 4,081,319 and 4,200,488 disclose wet-laying techniques that may be used to practice the present invention.

Once good formation is achieved, the web is ready for hydroentanglement. A typical hydroentanglement process and suitable apparatus for the practice of this invention are disclosed in U.S. Pat. No. 3,508,308, incorporated herein by reference. After the fibers have been entangled together, the nonwoven web of the present invention is dried without the addition of a bonding agent.

The objective of hydroentanglement is to ensure that the web will have sufficient wet strength for use and yet be capable of disintegrating under mild agitation in water. Preferably, the web is minimally entangled with as few manifold passes as possible at relatively low pressure. The hydroentanglement treatment entangles together the fibers forming the web such that only friction and any naturally occurring hydrogen bonding (characteristic of hydroxylic compounds, e.g. water-laid cellulose fibers) provide the necessary wet strength without addition of wet strength additives or bonding agents.

U.S. Pat. No. 3,485,706, incorporated herein by reference, discusses the theory of hydroentanglement in terms of energy expended per pound of web. The energy imparted to the hydroentangled web of the present invention can be calculated according to the following equation:

$$E = 0.125(YPQ/sb)N$$

where:
- E = Energy, horsepower-hours per pound of web
- Y = Number of orifices per linear inch of manifold
- P = Pressure of water in manifold, psig
- Q = Volumetric flow rate of water, cubic feet per minute per orifice
- s = Speed of conveyor to pass web under water streams, feet per minute
- b = Weight of web, ounces per square yard
- N = Number of entanglement passes Total energy required to treat the web of this invention can be in the range of about 0.007 to 0.090 horsepower-hours per pound of web. Preferably, the range is about 0.013 to 0.035 horsepower-hours per pound.

A typical hydroentanglement condition for the nonwoven web of the present invention is a multi-step application of jetted water to the web, traveling at 240 feet per minute, of two passes at 200 psig plus four passes at 400 psig providing a total supplied energy of 0.0218 horsepower-hours per pound of web.

In accordance with the present invention, a nonwoven web having a basis weight in the range of about 20 to 90 grams per square meter can be prepared from a very uniform mixture of about 5 to 30 weight percent short, staple length regenerated cellulose fibers and about 70 to 95 weight percent wood pulp fibers which has been hydroentangled with water jets to obtain a wet tensile strength of at least about 250 grams/inch.

The regenerated cellulose fibers can have a denier of about 6.0 or less and an average length in the range of about 7 to 19 millimeters. Fibers with smaller denier are usually easier to hydroentangle than fibers with larger denier. Preferably these fibers have a denier of 3.0 or less and an average length in the range of 10 to 16 millimeters.

A preferred nonwoven fibrous web of this invention is a web having a basis weight of 72.9 grams per square meter comprising 85 weight percent Northern bleached softwood kraft (NBSK), and 15 weight percent of 1.5 denier × 10 millimeter rayon. This web was hydroentangled with columnar streams of water by moving it at 240 feet per minute under an entanglement header for two passes at 200 psig followed by four passes at 400 psig. The entanglement header had an orifice strip containing 40 holes per inch of 0.005 inch openings. Total entanglement energy input to this web was 0.0218 horsepower-hours per pound of substrate. Performance of this material was measured as follows:

Wet Tensile: 362 grams/1-inch strip (MD); 341 grams/1-inch strip (CD)

Breakup Time: 1.5 minutes

The following examples are provided as some illustrations of the present invention but they are not to be construed as limiting the invention to the specific details thereof.

EXAMPLES 1 THRU 20

In these examples, wet tensile strength and breakup time measurements were performed in accordance with U.S. Pat. No. 4,117,187. Handsheet samples of the particular fiber furnish were prepared by conventional wet-laying techniques. Then the fibers of these samples were entangled hydraulically by processing the handsheets on a hydroentanglement unit consisting of: (1) conveyor speed of 240 feet/minute, (2) jet hole diameter of 0.005 inch, (3) jet density of 40 orifices per inch, (4) entanglement at 200 psig for first two headers and 400 psig for next four headers (six headers total) and (5) 100 mesh polyester backing screen. For wet tensile strength, the dry substrate was initially cut into 1"×4" strips. These strips were then immersed in water, blotted between paper towels, and tested. Breakup time was the time measured from the beginning of agitation, until the wiper was broken down to pieces smaller than 0.75 inch in diameter. The elapsed time required to obtain the specified degree of breakup was recorded for each test.

TABLE I
Wet Tensile Strength And Breakup Time For Various Furnishes

| Furnish | CD Wet Tensile (grams/inch) | Breakup Time (minutes) |
| --- | --- | --- |
| 1. 85% NBSK softwood, 15% 1.5 d × 7 mm rayon | 371 | 0.6 |
| 2. 85% NBSK softwood, 15% 1.5 d × 10 mm rayon | 341 | 1.5 |
| 3. 85% NBSK softwood, 15% 1.5 d × 12.5 mm rayon | 558 | 2.0 |
| 4. 85% NBSK softwood, 15% 1.5 d × 14 mm rayon | 544 | 2.25 |
| 5. 82.5% NBSK softwood, 17.5% 1.5 d × 7 mm rayon | 344 | 0.6 |
| 6. 82.5% NBSK softwood, 17.5% 1.5 d × 10 mm rayon | 473 | 1.5 |
| 7. 82.5% NBSK softwood, 17.5% 1.5 d × 12.5 mm rayon | 694 | 2.0 |
| 8. 82.5% NBSK softwood, 17.5% 1.5 d × 14 mm rayon | 628 | 2.25 |
| 9. 80% NBSK softwood, 20% 1.5 d × 7 mm rayon | 430 | 0.6 |
| 10. 80% NBSK softwood, 20% 1.5 d × 10 mm rayon | 597 | 1.5 |
| 11. 80% NBSK softwood, 20% 1.5 d × 12.5 mm rayon | 706 | 2.0 |
| 12. 80% NBSK softwood, 20% 1.5 d × 14 mm rayon | 764 | 2.25 |
| 13. 75% NBSK softwood, 25% 1.5 d × 7 mm rayon | 555 | 0.6 |
| 14. 75% NBSK softwood, 25% 1.5 d × 10 mm rayon | 676 | 1.5 |
| 15. 75% NBSK softwood, 25% 1.5 d × 12.5 mm rayon | 965 | 2.0 |
| 16. 75% NBSK softwood, 25% 1.5 d × 14 mm rayon | 868 | 2.25 |
| 17. 70% NBSK softwood, 30% 1.5 d × 12.5 mm rayon | 1330 | 2.5 |
| 18. 70% NBSK softwood, 30% cellulose acetate | 120 | 0.16 |
| 19. 70% NBSK softwood, 15% rayon, 15% cellulose acetate | 150 | 0.16 |
| 20. 70% NBSK softwood, 30% 19 mm hollow rayon | 704 | 1.33 |

Table II gives data listed in U.S. Pat. No. 4,117,187 for various webs, one having no binder and four webs having a pH sensitive binder.

TABLE II
U.S. Pat. No. 4,117,187 - Table V

| Na Acrysol ASE-75 in Dip, % | Acrysol Pickup, g./100 g. fiber | CD Wet Tensile grams/cm Dilute Acid | CD Wet Tensile grams/cm Tap Water | Breakup Time minutes |
| --- | --- | --- | --- | --- |
| None | — | 55 | — | 1 |
| 1 | 1.1 | 220 | 107 | 13 |
| 2 | 3.1 | 328 | 144 | 38 |
| 3 | 5.2 | 278 | 185 | 45 |
| 4 | 7.9 | 257 | 154 | 54 |

In contrast to the results listed in Table II the hydroentangled nonwoven web of the present invention demonstrates better wet strength with surprisingly better breakup performance.

EXAMPLES 21 THRU 32

Table III lists a range of wet tensile strength and breakup times obtainable under different hydroentanglement conditions for a web having a basis weight of 72.9 grams per square meter comprising 85 weight percent NBSK pulp and 15 weight percent of 1.5 denier × 10 millimeter rayon. Hydroentanglement conditions consisted of two passes under a header at 200 psig water pressure plus additional passes under the header at varying pressures as listed in the table. The header had a jet density of 40 orifices per inch with a jet hole diameter of 0.005 inch. All material was passed under the water header at a conveyer speed of 240 feet/minute on a polyester backing screen of 100 mesh. Wet tensile strength and breakup time measurements were performed in a manner similar to that described for examples 1 thru 20.

TABLE III

Wet Tensile Strength and Breakup Time for Varying Hydroentanglement Conditions

| Entanglement passes-pressure (no.) | (psig) | CD Wet Tensile (grams/inch) | Energy (hp-hr/lb) | Breakup Time (minutes) |
|---|---|---|---|---|
| 21. | 2 at 200 | 159 | 0.007 | 0.1 |
| 22. | 4 at 200 | 170 | 0.010 | 0.1 |
| 23. | 6 at 200 | 208 | 0.013 | 0.2 |
| 24. | 2 at 400 | 273 | 0.013 | 0.5 |
| 25. | 4 at 400 | 369 | 0.022 | 1.0 |
| 26. | 6 at 400 | 390 | 0.031 | 1.1 |
| 27. | 2 at 600 | 403 | 0.020 | 1.1 |
| 28. | 4 at 600 | 453 | 0.037 | 1.3 |
| 29. | 6 at 600 | 411 | 0.054 | 2.3 |
| 30. | 2 at 800 | 540 | 0.029 | 1.5 |
| 31. | 4 at 800 | 521 | 0.056 | 3.2 |
| 32. | 6 at 800 | 457 | 0.082 | 4.6 |

As is seen in Table III, there is a trade-off between wet tensile strength and breakup time of the material. Generally, breakup time increases as more hydroentanglement energy is imparted to the web. Conversely, for lower breakup times less hydroentanglement energy is necessary and wet tensile strength is reduced. Suprisingly, the hydroentangled nonwoven web of the present invention shows excellent wet strength (at least 250 grams/inch) with a far lower breakup time (less than 2.5 minutes) than the prior art fabrics.

This invention gives a superior product with cloth-like hand and rapid breakup time at higher wet tensile strengths and opens up a wide range of applications for hydroentangled flushable materials.

It will be apparent to those skilled in the art that various modifications and variations can be made in the products of the present invention without departing from the scope or spirit of the invention. Thus we intend that such modifications and variations are covered by the present invention as they come within the scope of the following claims and their equivalents.

What is claimed is:

1. A nonwoven fibrous web having a basis weight in the range of 20 to 90 grams per square meter, said web being characterized by sufficient wet strength in an aqueous environment to enable its use as a wet wiper and by being capable of disintegrating under mild agitation in water and decomposing in a septic system, which web comprises at least 70 weight percent wood pulp fibers and at least 5 weight percent short staple length regenerated cellulose fibers, said fibers being hydroentangled together to form a composite web having a wet tensile strength of at least 250 grams per inch.

2. A nonwoven fibrous web as defined in claim 1 wherein the web has a basis weight in the range of 60 to 75 grams per square meter and comprises 70 to 95 weight percent softwood papermaking fibers and 5 to 30 weight percent regenerated cellulose fibers.

3. A nonwoven fibrous web as defined in claim 1 wherein the web has a basis weight in the range of 60 to 75 grams per square meter and comprises 80 to 90 weight percent softwood papermaking fibers and 10 to 20 weight percent regenerated cellulose fibers.

4. A nonwoven fibrous web as defined in claim 1 wherein the regenerated cellulose fibers are rayon fibers.

5. A nonwoven fibrous web as defined in claim 1 wherein the regenerated cellulose fibers are hollow rayon fibers.

6. A nonwoven fibrous web as defined in claim 1 wherein the regenerated fibers have a denier of 6.0 or less and an average length in the range of 7 to 19 millimeters.

7. A nonwoven fibrous web as defined in claim 1 wherein the regenerated cellulose fibers have a denier of 3.0 or less and an average length in the range of 10 to 16 millimeters.

8. A nonwoven fibrous web as defined in claim 1 wherein the web is wet-laid.

9. A nonwoven fibrous web as defined is claim 1 wherein the web is dry-laid.

10. A nonwoven fibrous web comprising about 70 to 95 weight percent pulp fibers selected from the group consisting of spruce, hemlock, cedar, pine, and sisal fibers and blends thereof, and about 5 to 30 weight percent synthetic fibers having a denier of 6.0 or less and an average length in the range of 7 to 19 millimeters selected from the group consisting of rayon, hollow rayon, cellulose acetate, chitin, polyester, polyolefin, polysaccharide, and nylon acrylic fibers and blends thereof, hydroentangled together to form a composite web having a wet tensile strength of at least 250 grams/inch.

11. A method of forming a nonwoven fibrous web having a basis weight in the range of 20 to 90 grams per square meter and sufficient wet strength in an aqueous environment for use as a wet wiper capable of disintegrating under mild agitation in water and decomposing in a septic system, comprising:
(a) forming a dispersion consisting essentially of 5 to 30 weight percent short staple length regenerated cellulose fibers and 70 to 95 weight percent softwood papermaking fibers in an aqueous carrier medium;
(b) forming a wet web of the fibers on a foraminous member;
(c) entangling the fibers in the web with one another by hydroentanglement with sufficient energy to impart a wet tensile strength of at least 250 grams per inch to the web; and,
(d) drying the web without the addition of a bonding agent.

12. A method of forming a nonwoven fibrous web as defined in claim 11 wherein the energy expended to entangle the fibers is in the range of about 0.007 to 0.090 horsepower-hours per pound of web.

13. A method of forming a nonwoven fibrous web as defined in claim 12 wherein the energy expended to entangle the fibers is in the range of about 0.013 to 0.035 horsepower-hours per pound of web.

* * * * *